United States Patent [19]
Johnson

[11] Patent Number: 5,990,111
[45] Date of Patent: Nov. 23, 1999

[54] ALDOSE REDUCTASE INHIBITION IN PREVENTING OR REVERSING DIABETIC CARDIOMYOPATHY

[75] Inventor: Brian F. Johnson, East Lyme, Conn.

[73] Assignee: Pfizer Inc., New York, N.Y.

[21] Appl. No.: 09/071,589

[22] Filed: May 1, 1998

Related U.S. Application Data

[60] Provisional application No. 60/045,822, May 5, 1997.

[51] Int. Cl.⁶ .......................... A61K 31/50; A61K 31/425
[52] U.S. Cl. .......................... 514/252; 514/365; 514/366; 514/367; 514/866
[58] Field of Search .................................. 514/252, 365, 514/366, 367, 866

[56] References Cited

U.S. PATENT DOCUMENTS

| | | | |
|---|---|---|---|
| 4,743,611 | 5/1988 | Malamas et al. | 514/390 |
| 4,748,280 | 5/1988 | Mylari et al. | 568/595 |
| 4,868,301 | 9/1989 | Mylari et al. | 544/237 |
| 5,064,830 | 11/1991 | Going | 514/252 |
| 5,164,391 | 11/1992 | Kurono et al. | 514/253 |
| 5,304,557 | 4/1994 | Mylari | 514/248 |
| 5,728,704 | 3/1998 | Mylari et al. | 514/256 |
| 5,834,466 | 11/1998 | Ramasamy et al. | 514/227.5 |

OTHER PUBLICATIONS

Chemical Abstracts (126:16897d) Ramasamy et al. (1997).
Zarich et al., American Heart Journal, vol. 118, pp. 1000–1012 (1989).
Cameron et al., Diabetologia, vol. 32, pp. 365–370 (1989).
Roy et al., Diabetes Research and Clinical Practice, vol. 10, pp. 91–97 (1990).
Raev, D. C., *Clinical Cardiology*, "Evolution of Cardiac Changes in Young Insulin–Dependent (Type 1) Diabetic Patients–One More Piece of the Puzzle of Diabetic Cardiopathy", 1993, vol. 16, pp. 784–790.
Spector, K.S., *Clinical Cardiology*, "Diabetic Cardiomyopathy", 1998, vol. 21, pp. 885–887.

*Primary Examiner*—Kevin E. Weddington
*Attorney, Agent, or Firm*—Peter C. Richardson; Gregg C. Benson; Carl J. Goddard

[57] ABSTRACT

This invention relates to the use of aldose reductase inhibitors in the treatment, prevention or reversal of diabetic cardiomyopathy in a human subject.

12 Claims, No Drawings

ALDOSE REDUCTASE INHIBITION IN PREVENTING OR REVERSING DIABETIC CARDIOMYOPATHY

CROSS REFERENCE TO RELATED APPLICATIONS

This application claims priority from Provisional Application No. 60/045,822, filed May 5, 1997.

FIELD OF THE INVENTION

This invention relates to the use of aldose reductase inhibitors in the treatment or reversal of diabetic cardiomyopathy in a human subject.

BACKGROUND OF THE INVENTION

Of all identified diabetic sequelae, perhaps the most physiologically deleterious are those complications involving the cardiovascular system. These may, for example, involve the blood or nervous supply to the heart or the heart muscle (myocardium) directly. An associated disease state related to myocardial abnormalities is diabetic cardiomyopathy, an affliction in which subjects afflicted therewith manifest such symptomes as, inter alia, an overall reduction in cardiac performance, reduced ventricular compliance as characterized by slowed, incomplete cardiac filling (diastolic dysfunction), an increased incidence of congestive heart failure and a markedly enhanced potential for death during episodes of myocardial infarction. Moreover, secondary indicators such as the development of interstitial and myocellular tissue abnormalities (including interstitial, perivascular and focal scar-like connective tissue accumulations) may be present in addition to microangiopathy (including thickening of the capillary basement membrane, pericapillary edema and capillary microaneurysms). These characteristic abnormalities define the syndrome of diabetic cardiomyopathy. Detailed discussions of this condition may be found, for example, in F. S. Fein, et. al., "Diabetic Cardiomyopathy", Cardiovascular Drugs and Therapy, Vol. 8, pp. 65–73, 1994, and D. S. H. Bell, "Diabetic Cardiomyopathy", Diabetes Care, Vol. 18, pp. 708–714, 1995 and pertinent references cited therein.

Aldose reductase inhibitors constitute a class of compounds which have become well known for their utility in the treatment of certain diabetic complications such as ocular cataract formation and diabetic neuropathy and nephropathy. Such compounds are well known to those skilled in the art and may be identified by standard biological methodology.

The compound zopolrestat, 3,4-dihydro-4-oxo-3-(5-trifluoromethylbenzothiazol-2-ylmethyl)phthalazin-1-ylacetic acid, is known, for example, from commonly assigned U.S. Pat. No. 4,939,140, the disclosure of which is hereby incorporated by reference, together with a number of related compounds, as having utility as aldose reductase inhibitors. Zopolrestat has the structure

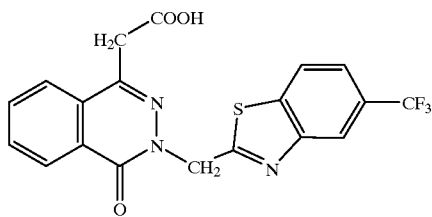

and, as an aldose reductase inhibitor, has utility in the treatment of certain complications arising from diabetes mellitus.

Other aldose reductase inhibitors are known to have use in the lowering of lipid levels in mammals, including humans. See, for example, U.S. Pat. No. 4,492,706 and EP 0 310 931 A2, as well as commonly assigned U.S. Pat. No. 5,391,551, the disclosures of which are also incorporated herein by reference.

Commonly assigned U.S. Pat. No. 5,064,830, the disclosure of which is hereby incorporated by reference, discloses the use of certain oxophthalazinyl acetic acids, including zopoirestat, for the lowering of blood uric acid levels.

SUMMARY OF THE INVENTION

This invention is directed to a method of treating, or reversing diabetic cardiomyopathy in a human subject. The method comprises administering to a human patient in need of such treatment or reversal, a therapeutically effective amount of an aldose reductase inhibitor.

Of particular interest in the practice of the method of the instant invention are certain compounds of structure (I), including zopolrestat, and their pharmaceutically acceptable salts as described hereinbelow.

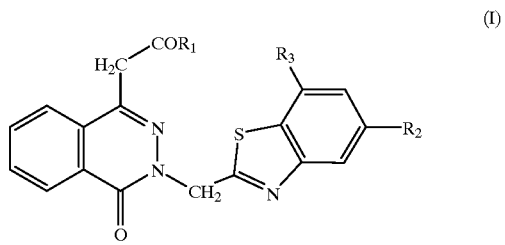

DETAILED DESCRIPTION OF THE INVENTION

Any aldose reductase inhibitor may be employed as the active agent in treating or reversing diabetic cardiomyopathy according to the method of this invention.

As employed herein, the term "treatment" is specifically intended to incorporate partial prevention or prevention which, although greater than that which would result from taking no drug or from taking placebo, is less than 100% in addition to complete or substantially complete prevention. Therefore, the active compound may be employed prophylactically to prevent, blunt or stem the onset of diabetic cardiomyopathy in those patients who are deemed to be at particular risk. Additionally, the term "reversal" is also intended to include partial reversal or reversal which, although greater than that resulting from taking no drug or placebo, is less than 100% in addition to complete or substantially complete reversal.

The term "aldose reductase inhibitor" refers to compounds which function by inhibiting the activity of the enzyme aldose reductase, which is primarily responsible for regulating the metabolic reduction of aldoses, like glucose or galactose, to their corresponding polyols, such as sorbitol and galactitol, in the body. Progressive, abnormal accumulation of these polyol metabolites in the tissues of diabetic patients is invariably associated with major complications such as neuropathy, ocular cataract formation, nephritis, nephropathy, etc.

A variety of aldose reductase inhibitors are disclosed and referenced below. However, additional aldose reductase inhibitors will also be known to those skilled in the art. Where applicable, the common USAN names or other designations are shown in parentheses, together with reference to the appropriate patent literature disclosing the compound. The disclosures of the U.S. patents listed below are hereby incorporated by reference.

1. 3-(4-bromo-2-fluorobenzyl)-3,4-dihydro-4-oxo-1-phthalazineacetic acid (ponalrestat, U.S. Pat. No. 4,251,528);
2. N-[6-methoxythio-5-(trifluoromethyl)-1-naphthoyl] sarcosine (toirestat, U.S. Pat. No. 4,600,724);
3. 5-[Z,E)-β-methylcinnamylidene]-4-oxo-2-thioxo-3-thiazolideneacetic acid (epairestat, U.S. Pat. No. 4,464,382, 4,791,126, and U.S. Pat. No. 4,831,045);
4. 3-(4-bromo-2-fluorobenzyl)-7-chloro-3,4-dihydro-2,4-dioxo-1(2H)-quinazolineacetic acid (zenarestat, U.S. Pat. No. 4,734,419, and U.S. Pat. No. 4,883,800);
5. 2R,4R-6,7-dichloro-4-hydroxy-2-methylchroman-4-acetic acid (U.S. Pat. No. 4,883,410);
6. 2R,4R-6,7-dichloro-6-fluoro-4-hydroxy-2-methylchroman-4-acetic acid (U.S. Pat. No. 4,883,410);
7. 3,4-dihydro-2,8-diisopropyl-3-oxo-2H-1,4-benzoxazine-4-acetic acid (U.S. Pat. No. 4,771,050);
8. 3,4-dihydro-3-oxo-4-[(4,5,7-trifluoro-2-benzothiazolyl)methyl]-2H-1,4-benzothiazine-2-acetic acid (SPR-210, U.S. Pat. No. 5,252,571);
9. N-[3,5-dimethyl-4-[(nitromethyl)sulfonyl]phenyl]-2-methyl-benzeneacetamide (ZD 5522, U.S. Pat. No. 5,270,342 and U.S. Pat. No. 5,430,060);
10. (S)-6-fluorospiro[chroman-4,4'-imidazolidine]-2,5'-dione (sorbinil, U.S. Pat. No. 4,130,714);
11. d-2-methyl-6-fluoro-spiro(chroman-4', 4'imidazolidine)-2',5'-dione (U.S. Pat. No. 4,540,704);
12. 2-fluoro-spiro(9H-fluorene-9,4'-imidazolidine)-2',5'-dione (U.S. Pat. No. 4,438,272);
13. 2,7-di-fluoro-spiro(9H-fluorene-9,4'-imidazolidine)-2',5'-dione (U.S. Pat. No. 4,436,745, and U.S. Pat. No. 4,438,272);
14. 2,7-di-fluoro-5-methoxy-spiro(9H-fluorene-9,4'-imidazolidine)-2',5'-dione (U.S. Pat. No. 4,436,745, and U.S. Pat. No. 4,438,272);
15. 7-fluoro-spiro(5H-indenol[1,2b]pyridine-5,3'-pyrrolidine)-2,5'-dione (U.S. Pat. No. 4,436,745, and U.S. Pat. No. 4,438,272);
16. d-cis-6'-chloro-2',3'-dihydro-2-'methyl-spiro-(imidazolidine-4,4'-4'-H-pyrano(2,3-b)pyridine)-2,5-dione (U.S. Pat. No. 4,980,357);
17. spiro[imidazolidine-4,5'-(6H)-quinoline]-2,5-dione-3'-chloro-7',8'-dihydro-7'-methyl-(5'-cis) (U.S. Pat. No. 5,066,659);
18. (2S,4S)-6-fluoro-2',5'-dioxospiro(chroman-4,4'-imidazolidine)-2-carboxamide (U.S. Pat. No. 5,447,964); and
19. 2-[(4-bromo-2-fluorophenyl)methyl]-6-fluoro-spiro [isoquinoline-4-(1H), 3'-pyrrolidine]-1,2',3,5'-(2H)-tetrone (WAY-121509, U.S. Pat. No. 5,037,831).

Other compounds useful in the method of this invention are those compounds of formula (I) or the pharmaceutically acceptable salts thereof, wherein $R_1$ is hydroxy or a prodrug group capable of being removed in vivo to form a compound of formula (I) wherein $R_1$ is hydroxy; and $R_2$ and $R_3$ are the same or different and are selected from the group consisting of hydrogen, trifluoromethyl, fluoro, chloro, and bromo.

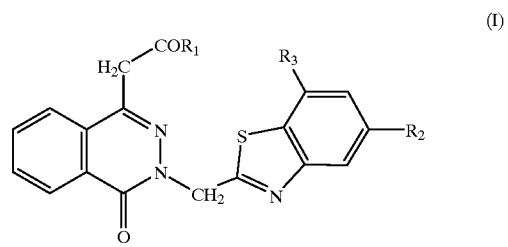

Specific compounds of formula (I) which are particularly useful in the method provided by this invention include (with reference to values in formula (I) shown in brackets): 3,4-dihydro-4-oxo-3-(5-trifluoromethylbenzothiazol-2-ylmethyl)phthalazin-1-ylacetic acid ($R_1$ is OH; $R_2$ is $CF_3$ and $R_3$ is H); 3,4-dihydro-4-oxo-3-(5-fluorobenzothiazol-2-ylmethyl)phthalazin-1-ylacetic acid ($R_1$ is OH; $R_2$ is F and $R_3$ is H); 3,4-dihydro-4-oxo-3-(5-chlorobenzothiazol-2-ylmethyl)phthalazin-1-ylacetic acid ($R_1$ is OH; $R_2$ is Cl and $R_3$ is H); 3,4-dihydro-4-oxo-3-(5-bromobenzothiazol-2-ylmethyl)phthalazin-1-ylacetic acid ($R_1$ is OH; $R_2$ is Br and $R_3$ is H); 3-(5,7-difluorobenzothiazol-2-ylmethyl)-3,4-dihydro-4-oxophthalazin-1-ylacetic acid ($R_1$ is OH; $R_2$ and $R_3$ are both F); 3-(5,7-dichlorobenzothiazol-2-ylmethyl)-3,4-dihydro-4-oxophthalazin-1-ylacetic acid ($R_1$ is OH; $R_2$ and $R_3$ are both Cl); 3-(5,7-bistrifluoromethylbenzothiazol-2-ylmethyl)-3,4-dihydro-4-oxophthalazin-1-ylacetic acid ($R_1$ is OH; $R_2$ and $R_3$ are both $CF_3$). Zopolrestat (3,4-dihydro-4-oxo-3-(5-trifluoromethylbenzothiazol-2-ylmethyl)phthalazin-1-ylacetic acid ($R_1$ is OH; $R_2$ is $CF_3$; $R_3$ is H)) is particularly preferred.

Prodrug groups which are capable of being removed in vivo to produce a compound of formula (I), wherein $R_1$ is OH are generally known to those skilled in the art and may include, for example, ester-forming groups such as benzyloxy, di($C_1$–$C_4$)alkylaminoethyloxy, acetoxymethoxy, pivaloyloxymethoxy, phthalidoyl, ethoxycarbonyloxyethoxy, 5-methyl-2-oxo-1,3-dioxol-4-ylmethoxy, ($C_1$–$C_4$)alkoxy optionally-substituted by morpholino and amide-forming groups such as di($C_1$–$C_4$) alkylamino.

Preparative methods for synthesizing compounds of formula (I) which include such particulars as solvents, temperatures, catalysts and procedures for making and/or sources of precursor compounds may be obtained from the teachings of the aforementioned U.S. Pat. No. 4,939,140 as well as the commonly assigned U.S. Pat. No. 4,868,301, the disclosure of which is also incorporated herein by reference.

Some of the compounds useful in the method of this invention have asymmetric carbon atoms and therefore may exist in enantiomeric or diastereomeric configurations. Diastereomeric mixtures may be separated, if necessary, into their individual diastereomers on the basis of their physicochemical differences by methods known per se, for example, by chromatography and/or fractional crystallization.

Those skilled in the art will appreciate that many aldose reductase inhibitors, especially those compounds of formula (I) where $R_1$ is OH, may form basic addition salts, and such pharmaceutically acceptable basic addition salts are intended to be within the scope of this invention. Pharmaceutically acceptable basic addition salts of compounds of formula (I) may be formed with pharmaceutically acceptable cations by conventional methods. For instance, such salts may be prepared readily by treating a compound of formula (I) with an aqueous solution of the hydroxide of the desired pharmaceutically acceptable cation and then evaporating the resulting solution to dryness, preferably under reduced pressure. Alternatively, a lower alkyl alcohol solution of a compound of formula (I) may be mixed with an alkoxide of a desired metal cation and the solution subsequently evaporated to dryness. Suitable pharmaceutically acceptable cations for this purpose may include, but are not limited to, alkali metal cations such as potassium and sodium, ammonium or water-soluble amine addition salts such as N-methylglucamine (meglumine), the lower alkanolammonium and other base salts with organic amines which are pharmaceutically acceptable, and alkaline earth metal cations such as calcium and magnesium. In general, the sodium and N-methylglucamine salts are preferred.

It will also be appreciated that pharmaceutically acceptable acid addition salts may be formed with certain aldose reductase inhibitors of this invention and such acid addition salts are also intended to be included within the scope of the instant invention. These pharmaceutically acceptable acid addition salts may be formed by conventional techniques by treating a solution or suspension of the free base of a compound with about one chemical equivalent of a pharmaceutically acceptable acid. Isolation of the acid addition salts prepared in this manner is most conveniently accomplished by conventional concentration and recrystallization techniques. Representative of such pharmaceutically acceptable acid addition salts include acetic, lactic, succinic, maleic, tartaric, citric, gluconic, ascorbic, benzoic, cinnamic, fumaric, sulfuric, phosphoric, hydrochloric, hydrobromic, hydriodic, sulfamic, sulfonic such as methanesulfonic, benzenesulfonic, and other related acids.

Some of the aforementioned compounds, including those of structure (I) may, under appropriate conditions, form solvates or hydrates and such compounds are also intended to be included within the scope of this invention.

The method of employing known aldose reductase inhibitors in accordance with the objectives of the instant invention, including aldose reductase inhibitors of formula (I), comprises administering to a human subject a therapeutically effective amount of such compound. Such administration comprises any known method for therapeutically providing an active compound to a human subject including such conventional routes as oral, transdermal, intraduodenal, or parenteral administration. For purposes of the method of the present invention, oral administration is generally preferred. In carrying out the objectives of the method of this invention, an amount of the aldose reductase inhibitor that is effective for treating or reversing diabetic cardiomyopathy is employed. Typically, an effective dose for the aldose reductase inhibitors of this invention is in the range of from about 0.1 mg per day to about 1,000 mg per day in either single (e.g., once-daily) or multiple doses. Preferred dosage ranges for compounds of formula (I), including zopolrestat, are from about 250 mg per day to about 1,000 mg per day in a single, oral dose. However, some variation in dosage will be necessary depending upon the condition of the patient being treated. In any event, the person responsible for administration will determine the appropriate dosage amount for the individual subject requiring treatment.

In the method of this invention, at least one active compound is employed, either individually, together in combination with another aldose reductase inhibitor or in combination with a pharmaceutically acceptable carrier. Suitable carriers may include solid diluents or fillers, sterile aqueous solutions and various physiologically compatible organic solvents. The pharmaceutical compositions formed by combining the active compound and the pharmaceutically acceptable carriers are then readily administered in a variety of dosage forms such as tablets, powders, lozenges, syrups, injectable solutions and so forth. These pharmaceutical compositions may, if desired, contain additional ingredients such as flavorings, binders, excipients, and the like. For purposes of the preferred route of oral administration, tablets containing various excipients such as sodium citrate, calcium carbonate and calcium phosphate may be used along with various disintegrants such as starch, alginic acid and certain complex silicates, together with binding agents such as polyvinylpyrrolidone, sucrose, gelatin, and acacia. Additionally, lubricating agents such as magnesium stearate, sodium lauryl sulfate, and talc are often useful for tabletting purposes. Solid compositions of a similar type may also be used as fillers in soft and hard filled gelatin capsules. Preferred materials for this use include lactose or milk sugar and high molecular weight polyethylene glycols. When aqueous suspensions or elixirs are desired for oral administration, the essential active ingredient therein may be combined with various sweetening or flavoring agents, coloring matter or dyes and, if desired, emulsifying or suspending agents, together with diluents such as water, ethanol, propylene glycol, glycerine and various combinations thereof.

For parenteral administration, solutions of the compounds useful in the method of this invention, including those of formula (I), in sesame or peanut oil, aqueous propylene glycol, or in aqueous solution may be employed. Such aqueous solutions should be suitably buffered if necessary and the liquid diluent first rendered isotonic with sufficient saline or glucose. These particular aqueous solutions are especially suitable for intravenous, intramuscular, subcutaneous and intraperitoneal administration. In this connection, the sterile aqueous media employed are all readily available by standard techniques known to those skilled in the art.

The in vivo utility of aldose reductase inhibitors in the treatment of human diabetic cardiomyopathy according to the method of this invention can be demonstrated by a randomized, double-blind, placebo-controlled clinical trial utilizing zoplorestat as the active agent.

In this study, both male and female patients between 18 and 65 years of age having demonstrated diabetes mellitus as defined by World Health Organization criteria (W.H.O. 1980/85 Technical Report Series No. 646/727) were initially evaluated for evidence of impaired cardiac performance indicative of diabetic cardiomyopathy.

Accordingly, a placebo-controlled, single-blind baseline evaluation was performed on prospective patients over a four week period utilizing the determination of heart rate variability during controlled respiration, and during a Valsalva test, and radionuclide ventriculography using multigated acquistion (MUGA) methodology (B. L. Holman, "Heart Disease", 3rd Edition, Chapter 11).

Radioventriculogram (RVG) determinations were made at rest, and during selected stages of exertion using a bicycle system suitable for use during ventriculography. Indicators of greatest importance were those involving rate of filling into and ejection of blood from the left ventricle, systolic and end diastolic volume of the left ventricle, calculated stroke volume, ejection fraction and cardiac output. The assessment of left ventricular volumes adds important complimentary information to the measurement of systolic and diastolic function. Absolute ventricular volumes were calculated according to the method of Massardo, et. al., J. Nucl. Med., Vol. 31, pp. 450–456, 1990. To be admitted into the double-blind phase, each patient must have demonstrated either a peak filling rate below 3 EDV(End Diastolic Volume)/sec, resting systolic ejection fraction (EF) below 50% of EDV, or a subnormal increase in left ventricular ejection fraction between resting and maximal level of exertion.

The degree of impairment of cardiac autonomic activity may be shown by a reduction in the normal variability of EKG R—R interval, most obviously, during respiration. The standard deviation of the mean R—R interval for a five-minute period during quiet breathing is a commonly used method of determining R—R variation, which is primarily a measure of parasympathetic nervous system activity. See, for example, T. Roy, et. al., Am. J. Med., Vol. 87, pp. 382–388, 1989. The Valsalva test (Gorlin, et. al., Am. J. Med., Vol. 22, pp. 197–203, 1957) is a cardiovascular test that relies upon evaluation of cardiac responses during and after a standardized increase in intrathoracic pressure (Valsalva maneuver). An abnormally low Valsalva ratio (the fastest heart rate during the Valsalva maneuver divided by the slowest heart rate after the Valsalva maneuver) may be due either to decreased cardiac parasympathetic or decreased cardiac or vascular sympathetic tone. Thus, it serves as a general autonomic test. Subjects with or without evidence of impaired cardiac autonomic activity were studied.

A stress thallium test was also performed with concurrent determination of EKG changes to preclude participation of any patient presenting unequivocal evidence of coronary artery disease. Prospective patients exhibiting such evidence were withdrawn from the study.

The single-blind placebo baseline evaluation was followed by a double-blind period of 52 weeks duration during which patients were randomly assigned to a treatment regimen consisting of either placebo, zopolrestat 500 mg once daily, or zopolrestat 1,000 mg once daily.

The evaluation of peak ejection fraction endpoints as determined by radionuclide ventriculography was conducted at weeks 4, 16 and 52 of the double-blind period.

As shown in Table 1 below, the treatment of patients with zopolrestat at 500 mg (zopolrestat B) and 1,000 mg (zopolrestat C) dosages resulted in a significant improvement in the ventricular peak ejection fraction during exercise as compared to placebo. Specifically, the baseline placebo group deteriorated over the 52 week period of study while the two zopolrestat groups exhibited higher ventricular peak ejection fraction than placebo. This indicates the utility of zopolrestat in both preventing the deterioration of cardiac function, and in reversing established abnormality.

TABLE 1

Mean Response from Radionuclide Ventriculography Zopolrestat

| Endpoint | Treatment | N | Week 52 Observed | Baseline |
|---|---|---|---|---|
| Max. Diff. on | Placebo | 18 | 6.36 (8.04) | 10.44 (7.11) |
| Ejection Fraction | Zopolrestat B | 18 | 9.27 (6.19) | 6.14 (8.27) |
| (%) | Zopolrestat C | 20 | 7.97 (6.89) | 4.05 (9.61) |
| Max. Ejection | Placebo | 18 | 64.50 (10.19) | 67.55 (8.02) |
| Fraction at | Zopolrestat B | 18 | 71.22 (5.59) | 65.89 (7.60) |
| Exercise (%) | Zopolrestat C | 20 | 68.65 (8.30) | 66.10 (8.68) |

As shown in Table 2 below, this improvement in the maximum differential of ejection fraction at exercise is statistically significant.

TABLE 2

Treatment Comparison in Radionuclide Ventriculography Zopolrestat

| Endpoint | Week | N | Placebo vs. Zopolrestat | Placebo vs. Zopolrestat B | Placebo vs. Zopolrestat C | Zopolrestat B vs Zopolrestat C |
|---|---|---|---|---|---|---|
| Max. Diff. on | 52 | 56 | 0.0078 | 0.0153 | 0.0223 | NS |
| Ejection Fraction | 16 | 63 | NS | NS | NS | NS |
| (%) | 4 | 75 | NS | NS | NS | NS |
| Max. Ejection | 52 | 56 | 0.0011 | 0.0007 | 0.0194 | 0.2032 |
| Fraction at | 16 | 63 | 0.0943 | 0.0698 | NS | NS |
| Exercise (%) | 4 | 75 | 0.0924 | 0.0570 | NS | NS |

All determinations of statistical significance were derived from an analysis of covariance (ANCOVA) model with baseline response as covariate and treatment terms. Such statistical methodology is well known to those skilled in the art. See, for example, A. A. Afifi, et. al, Statistical Analysis—A Computer Oriented Approach, 2nd Ed., pp. 262–274, (1979).

I claim:

1. A method of treating diabetic cardiomyopathy in a human subject in need of such treatment which comprises administering a therapeutically effective amount of an aldose reductase inhibitor to said human subject.

2. A method as claimed in claim 1 wherein said aldose reductase inhibitor is a compound of structural formula I

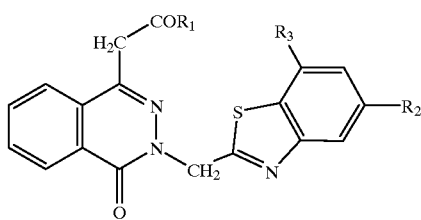

(I)

or a pharmaceutically acceptable salt thereof, wherein $R_1$ is OH or a prodrug group capable of being removed in vivo to produce a compound of formula I wherein $R_1$ is OH; and $R_2$ and $R_3$ are the same or different and are selected from the group consisting of hydrogen, trifluoromethyl, fluoro, chloro and bromo.

3. A method as claimed in claim 2 wherein said compound I is selected from the group consisting of 3,4-dihydro-4-oxo-3-(5-trifluoromethylbenzo-thiazol-2-ylmethyl) phthalazin-1-ylacetic acid, 3,4-dihydro-4-oxo-3-(5-fluorobenzothiazol-2-ylmethyl)phthalazin-1-ylacetic acid, 3,4-dihydro-4-oxo-3-(5-chlorobenzothiazol-2-ylmethyl) phthalazin-1-yl acetic acid, 3,4-dihydro-4-oxo-3-(5-bromobenzothiazol-2-ylmethyl)phthalazin-1-yl acetic acid, 3-(5,7-difluorobenzothiazol-2-ylmethyl)-3,4-dihydro-4-oxophthalazin-1-ylacetic acid, 3-(5,7-dichlorobenzothiazol-2-ylmethyl)-3,4-dihydro-4-oxophthalazin-1-ylacetic acid, and 3-(5,7-bistrifluoromethylbenzothiazol-2-ylmethyl)-3,4-dihydro-4-oxophthalazin-1-ylacetic acid.

4. A method as claimed in claim 3 wherein said compound I is 3,4-dihydro-4-oxo-3-(5-trifluoromethylbenzothiazol-2-ylmethyl)phthalazin-1-yl acetic acid, zopolrestat.

5. A method as claimed in claim 1 wherein said administration is oral.

6. A method as claimed in claim 2 wherein said administration is oral.

7. A method as claimed in claim 3 wherein said administration is oral.

8. A method as claimed in claim 4 wherein said administration is oral.

9. A method as claimed in claim 1 wherein said treatment comprises prevention or reversal of said diabetic cardiomyopathy.

10. A method as claimed in claim 2 wherein said treatment comprises prevention or reversal of said diabetic cardiomyopathy.

11. A method as claimed in claim 3 wherein said treatment comprises prevention or reversal of said diabetic cardiomyopathy.

12. A method as claimed in claim 4 wherein said treatment comprises prevention or reversal of said diabetic cardiomyopathy.

* * * * *